(12) United States Patent
Balfour et al.

(10) Patent No.: US 11,819,218 B2
(45) Date of Patent: Nov. 21, 2023

(54) METHOD AND DEVICE FOR GENERATING INJECTABLE FOAM

(71) Applicant: PROVENSIS LIMITED, London (GB)

(72) Inventors: Carol Suzanne Balfour, London (GB); David Ian Faulkner, London (GB); Stafford Moss, London (GB); Thomas Wyss, London (GB); Rex Faithfull, London (GB); Thomas Ajao, London (GB)

(73) Assignee: PROVENSIS LIMITED, London (GB)

( * ) Notice: Subject to any disclaimer, the term of this patent is extended or adjusted under 35 U.S.C. 154(b) by 1302 days.

(21) Appl. No.: 16/320,591

(22) PCT Filed: Jul. 26, 2017

(86) PCT No.: PCT/IB2017/054537
§ 371 (c)(1),
(2) Date: Jan. 25, 2019

(87) PCT Pub. No.: WO2018/020436
PCT Pub. Date: Feb. 1, 2018

(65) Prior Publication Data
US 2019/0159786 A1    May 30, 2019

(30) Foreign Application Priority Data

Jul. 26, 2016 (GB) ..................... 1612925

(51) Int. Cl.
*A61B 17/00* (2006.01)
*A61B 17/12* (2006.01)
(Continued)

(52) U.S. Cl.
CPC .... *A61B 17/12186* (2013.01); *A61B 17/0057* (2013.01); *A61B 17/00491* (2013.01);
(Continued)

(58) Field of Classification Search
CPC ........ A61B 17/12186; A61B 17/12109; A61B 2017/00526; B01F 23/235; B01F 35/2111;
(Continued)

(56) References Cited

U.S. PATENT DOCUMENTS 4,474,680 A * 10/1984 Kroll ................. B01F 35/56
261/DIG. 26
6,572,084 B1    6/2003 Ivanovich et al.
(Continued)

FOREIGN PATENT DOCUMENTS

FR    2 903 594 A1    1/2008
GB    1 589 306 A1    5/1981
(Continued)

OTHER PUBLICATIONS

International Search Report for International Application No. PCT/IB2017/054537, dated Oct. 27, 2017 (two pages).
(Continued)

*Primary Examiner* — Anshu Bhatia
(74) *Attorney, Agent, or Firm* — Seager, Tufte & Wickhem, LLP

(57) ABSTRACT

The present invention relates to methods and devices for production of injectable foams, such as those used in the treatment of varicose veins and other venous disorders. The method requires the delivery or supply of foamable liquid sclerosing agent and a suitable gas or a gas mixture to a foam producing structure in which the liquid and gas are combined to produce foam, wherein the liquid is delivered independently of the delivery of gas. Devices for producing injectable foam comprise a foam producing structure in which liquid and gas are combined to produce foam, the structure comprising an inlet for liquid and gas and an outlet for foam; a liquid pathway in communication with the inlet;
(Continued)

and a gas pathway in communication with the inlet, characterised in that the liquid pathway comprises a means for delivering liquid through the liquid pathway independently of gas delivery through the gas pathway. In preferred embodiments, the delivery of liquid and/or gas is controlled with volumetric pumps.

19 Claims, 11 Drawing Sheets

(51) Int. Cl.

| | | |
|---|---|---|
| *A61J 3/00* | (2006.01) | |
| *B01F 35/83* | (2022.01) | |
| *B01F 35/71* | (2022.01) | |
| *B01F 35/21* | (2022.01) | |
| *B01F 23/235* | (2022.01) | |
| *B29C 44/60* | (2006.01) | |
| *A61M 5/20* | (2006.01) | |
| *B29C 44/02* | (2006.01) | |
| *B29K 105/04* | (2006.01) | |
| *B29L 31/00* | (2006.01) | |

(52) U.S. Cl.
CPC .. *A61B 17/12031* (2013.01); *A61B 17/12109* (2013.01); *A61B 17/12181* (2013.01); *A61J 3/00* (2013.01); *B01F 23/235* (2022.01); *B01F 35/2111* (2022.01); *B01F 35/7176* (2022.01); *B01F 35/83* (2022.01); *B01F 35/831* (2022.01); *B29C 44/60* (2013.01); *A61B 2017/00526* (2013.01); *A61B 2017/00893* (2013.01); *A61M 5/2053* (2013.01); *B29C 44/02* (2013.01); *B29K 2105/04* (2013.01); *B29L 2031/7534* (2013.01)

(58) Field of Classification Search
CPC .... B01F 35/7176; B01F 35/83; B01F 35/831; B29C 44/60; A61M 5/2053
See application file for complete search history.

(56) References Cited

U.S. PATENT DOCUMENTS

| | | | |
|---|---|---|---|
| 8,679,051 B2 | 3/2014 | Keenan et al. | |
| 2013/0037277 A1 | 2/2013 | Henry | |
| 2013/0118763 A1* | 5/2013 | Pace | B01F 23/291 |
| | | | 169/46 |
| 2013/0261538 A1 | 10/2013 | Miyazaki et al. | |
| 2015/0283523 A1* | 10/2015 | Clausen | B01F 23/2323 |
| | | | 261/50.3 |
| 2016/0166782 A1 | 6/2016 | Levy et al. | |
| 2016/0166996 A1* | 6/2016 | Burkley | B29B 7/7414 |
| | | | 261/37 |

FOREIGN PATENT DOCUMENTS

| | | |
|---|---|---|
| GB | 1589306 A | 5/1981 |
| JP | 63132827 A | 6/1988 |
| JP | 2010512899 A | 4/2010 |
| JP | 2011136192 A | 7/2011 |
| SU | 546350 A1 | 2/1977 |
| WO | 2002041872 A1 | 5/2002 |
| WO | 2005053776 A1 | 6/2005 |
| WO | 200604202 A1 | 5/2006 |
| WO | 2008075080 A1 | 6/2008 |
| WO | 2011139479 A3 | 11/2011 |
| WO | 2015162499 A2 | 10/2015 |

OTHER PUBLICATIONS

Written Opinion of the International Searching Authority for International Application No. PCT/IB2017/054537 (five pages).

* cited by examiner

METHOD AND DEVICE FOR GENERATING INJECTABLE FOAM

This application is a national stage filing under 35 U.S.C. § 371 of International Application No. PCT/IB2017/054537, filed on Jul. 26, 2017, which claims priority of British Patent Application No. 1612925.6, filed Jul. 26, 2016. The contents of these applications are each incorporated herein by reference.

The present invention relates to a method and device for producing injectable foam, which is suitable for intravenous or intra-arterial administration. The invention is suitable, in particular, to provide flexibility in the production of sterile, clinical grade injectable foam of different, predetermined densities and concentrations, which may be used in the treatment of different disorders including venous disorders such as spider and reticular veins, varicose veins, venous malformations and pelvic congestion syndrome.

Parenteral administration of foam provides many advantages in treating pathologies where local action of drugs or other medical substances is required (EP1424067B1). Foam can displace fluid from highly vascularised organs and from blood vessels, and its distribution within the circulatory system can be controlled by targeted administration and by retention in capillary beds. Fluid displacement decreases dilution of drugs or other medical substances in fluid and allow direct contact with a surface to be treated, e.g. a venous endothelial wall, and this improves treatment. Additionally, delivery of drugs or other medical substances dispersed on the surface of bubbles in foam causes their active surface to increase exponentially, so that a desired therapeutic effect can be achieved with smaller doses. Gas-filled bubbles can be used by the physician to image internal body structures using sonography, i.e. ultrasound, after injection of foam. Foam containing appropriately sized gas bubbles can also be delivered to restrict blood flow to target tissues, e.g. hepatic tumours, by delivered transarterial delivery.

The most widely used injectable foams are provided for intravenous administration in the treatment of venous disorders. In particular, sclerosing foam is used to treat disorders such as varicose veins. Production of such foam requires combining of a solution of sclerosing agent with gas until foam is formed. The concentration of sclerosant liquid used in producing foam is typically selected based on the intended indication, e.g. high concentrations of sclerosing agent (e.g. 1-5% polidocanol) are used in the treatment of large varicose veins and venous malformations whereas lower concentrations of sclerosing agents (e.g. 0.25-1% polidocanol) are typically used in the treatment of superficial spider and reticular veins.

Foam is traditionally generated in individual batches by a physician immediately prior to treatment. In the "Tessari" method, liquid and gas are drawn separately into two syringes, the two syringes are connected using a simple connector or three way tap, and the syringe contents are passed back and forth between the two syringes until foam is produced (Tessari (2000). Phlebologie 53(1); 129). This method allows the physician to produce foams of different densities (by selecting appropriate volumes of liquid and gas) with different concentrations of active pharmaceutical ingredient, typically a sclerosant, but the quality of foam can vary greatly between batches and physicians. Additionally, these "physician compounded" foams are typically made with air, over which safety concerns have been raised due to the high content of nitrogen in air, its poor solubility in blood and the potential for resulting gas embolism.

In a second method a high speed beating action with a brush is used to generate foam suitable for injection into a vein (EP-A-0656203 and U.S. Pat. No. 5,676,962 (Cabrera)). This foam differs from Tessari foam in that it is made with physiologically acceptable gas, which avoids the potential complications with air-based foams. However, it is a batch process and whilst this gives the physician flexibility in preselecting density of foam, the batch size is limited by the size of the vessel in which the foam is made and the process suffers from the same problem of variability between batches (and physicians).

Whilst both Tessari and Cabrera methods are flexible in allowing foams of different densities to be made, the foams are only stable for a short period of time and so can be inconvenient if multiple does of foam are required during a single treatment session.

The issue of foam variability has been addressed with pressurised canister systems, such as those described by WO 00/72821 and WO 02/41872. In these devices, liquid and gas are forced through a series of passageways to form foam when the valve on the pressurised container is opened. The resulting foam has defined characteristics (density, bubble size distribution and stability) which are reproducible each time the canister valve is activated. However, the canisters are prefilled with liquid and pressurised gas at the point of manufacture and, as a result, produce foam having predetermined properties that cannot be adjusted or controlled as may be desirable for treating different conditions.

An alternative system for producing foam is provided in WO 2008/075080, which describes a sealed flexible loop chamber in which foam is formed and continuously renewed as liquid and gas are circulated through a foam generating structure under the force of an external peristaltic pump. The chamber is pre-filled with liquid and gas and thus produces foam having a predetermined density and concentration that cannot be adjusted unless a different sealed chamber is available (or prepared).

The prior art methods and devices described above force the physician to select flexibility of foam concentration and density at the expense of consistency (Tessari, Cabrera) or to select the consistency that comes with a GMP-manufactured product but at the expense of flexibility (WO 00/72821, WO 02/41872 and WO 2008/075080) since the GMP devices use pre-filled volumes of liquid and gas, and they are therefore limited to the production of foam having predetermined properties. Production of foam with different properties requires recharging of the system or the use of a different device, which is inconvenient in the clinic, particularly where foams having different properties might be needed to treat a single patient. Accordingly, there remains a need to provide a system which has the flexibility to enable to physician to select the appropriate properties of foam for a particular indication but in a way that gives assurance that foam characteristics are consistent and reproducible every time foam is produced.

The present invention addresses this need by providing a method of generating foam in which the volumes of liquid and gas that are combined to form foam can be adjusted independently of each other. Delivery of liquid and gas into a foam producing structure are uncoupled so as to provide flexibility over density, concentration and volume of a desired foam, while ensuring that foam consistency and reproducibility is maintained as is necessary for approved pharmaceutical products and procedures. This provides the clinician with a single device to produce the desired foam in an appropriate volume, at an appropriate density and at a desired concentration for a particular patient/indication. The flexibility in selecting foam and controlling volume, density and concentration is provided without sacrificing foam reproducibility or safety.

Accordingly, in a first aspect, the present invention provides a method of producing injectable foam comprising delivering foamable liquid and gas to a foam producing structure in which the liquid and gas are combined to produce foam, characterised in that the liquid is delivered independently of the delivery of gas.

Foamable liquid and gas are delivered to a foam producing structure independently, and this allows the user to adjust the identities and the relative amounts of liquid and gas being combined to produce foam. This allows for foam properties to be adjusted as necessary so that different indications can be treated effectively without a need to recharge a device already in use or prepare a new device for use. It will be understood that the density of foam influences bubble size and the rheology of foam with higher density foam having smaller bubbles better able to travel through smaller needles, e.g. 32 G needles as used in sclerotherapy of spider and reticular veins. The physician is thereby provided with flexibility to select and adjust volume, density or concentration of foam without sacrificing the consistency of foam production or the safety of the foam produced.

Suitable foamable liquids are well known to the person skilled in the art, and when producing sclerosing foam they are typically solutions of polidocanol or sodium tetradecyl sulfate (STS), as these are approved for use in many territories and are widely available. Typically, such a sclerosant liquid is provided as an aqueous solution of polidocanol between 0.1% and 5% (w/v) and, preferably between 0.25% and 3%. In particular applications, for example for treating incompetence of the great saphenous vein (GSV), the sclerosant liquid is 1% (w/v) polidocanol.

Alternatively, foam can be used to deliver therapeutic agents in treatment of a variety of diseases where blood cannot be used as the vehicle of agent delivery or where the agent has a narrow therapeutic window and where maximum efficacy is needed with delivery of the minimum possible dose as close as possible to a target site, for example injecting anti-inflammatories or corticosteroids in foam can reduce the gastrointestinal risks which systemic administration can produce. Delivery of a therapeutic agent in foam is also beneficial where prolonged exposure the agent is required, for example vasodilator administration to an ischemic limb, antibiotic, chemotherapy or antiviral administration to abscesses or localised infections or local anaesthetic administration. Foam is also suitable for delivery of therapeutic agents into compartmental conditions, including, for example onychomycosis where it is difficult to achieve satisfactory results by systemic administration of antimycotic agents. Examples of therapeutic agents that can be administered in foam include vasodilators, cardiovascular drugs, antimycotics, anti-infectious agents, antibiotics, chemotherapeutic agents, sulphonamides, cytostatics, anaesthetics, anti-inflammatories, prostaglandins, corticosteroids, hormones, antiviral agents and fibrinolytics. Such therapeutics can be delivered in a foam that comprises an inert foaming agent.

Any gas that is tolerated in the vasculature may be used in the method of the invention, as is well known in the art. Nitrogen and/or room air may be tolerated in certain applications, but gases such as oxygen, carbon dioxide, helium, xenon and mixtures of these gases are particularly suitable. Oxygen, carbon dioxide and mixtures of oxygen and carbon dioxide are preferred. These gases are particularly well tolerated because oxygen is readily absorbed by haemoglobin of red blood cells and carbon dioxide is readily soluble in blood. Preferably the gas or gas mixture used contains less than 0.8% nitrogen to reduce the risk of gas embolism. Optionally, the therapeutic agent may be the gas itself which can be kept in contact with the appropriate location by delivery in a foam, for example Oxygen can be administered in a foam to treat gaseous gangrenes produced by anaerobic germs or serious ischaemia of the extremities.

The foam producing structure provides a means for combining liquid and gas to form foam by disrupting and/or restricting the flow of each. The foam producing structure is arranged such that substantially all of the liquid and gas delivered into it are passed through a series of openings arranged to create turbulent flow and mixing within it. The structure can comprise an element defining at least one passage of cross sectional area 1 $\mu m^2$ to 10 $mm^2$, preferably 10 $\mu m^2$ to 5 $mm^2$, more preferably 50 $\mu m^2$ to 2 $mm^2$, through which the liquid and gas are passed. The maximum dimension of the passage or passages is preferably between 0.1 $\mu m$ and 2 mm, more preferably between 1 $\mu m$ and 1 mm, more preferably between 2 $\mu m$ and 500 $\mu m$, still more preferably between 3 $\mu m$ an 100 $\mu m$, and even more preferably between 5 $\mu m$ and 20 $\mu m$. The passage or passages is/are preferably provided by at least one element comprising one or more meshes, screens or sinters. The structure can comprise two or more, and ideally 3, 4, 5 or 6 such elements, such that all liquid delivered into the structure is combined with all gas delivered to the structure, thereby ensuring that foam of the required density or concentration is formed. Preferably the said elements are spaced apart in the direction of liquid and gas flow by between 0.1 mm and 10 mm, preferably between 0.5 mm and 5 mm. In one particular embodiment the structure comprises four elements in the form of four Nylon 66 meshes held within an open-ended polypropylene casing. Such meshes typically have a diameter of 6 mm and have a 14% open area made up of 5 $\mu m$ pores, with the meshes spaced 3.5 mm apart.

Foamable liquid is delivered to the foam producing structure independently of the delivery of gas. This means that liquid and gas are delivered to the foam producing structure by separate and independently controllable driving forces. Such delivery to the foam producing structure can be achieved by any means that allows for independent delivery including, for example, the use a pressurised source of liquid. Advantageously this permits independent delivery without requiring complex engineering or moving parts. In particular embodiments the liquid can be delivered independently to the foam producing structure by a pump. This is desirable as it allows the user to directly control the volume of liquid being delivered without requiring monitoring of liquid pressure. The pump can be a peristaltic pump that does not directly contact the liquid being delivered. This has a low risk of liquid and foam contamination as neither contact the pump directly. Preferably the pump is a volumetric pump. Volumetric pumps, such as those used in insulin pump systems, deliver a predetermined volume of liquid with every pump stroke, and these pumps therefore allow the user very precise control over the delivery of liquid. An example of a volumetric pump that may be used in the invention is provided as a pump module in EP1677859.

Gas can be delivered to the foam producing structure by any suitable means that allows the user to control the volume of gas being delivered. This ensures that the user can produce foam having the required density. Preferably gas is delivered through a sealed conduit such that the composition and the volume of gas delivered can be accurately controlled. Gas can be delivered by a volumetric pump. This allows the user very precise control over the delivery of gas. Preferably the gas is delivered to the foam producing structure under pressure. This allows the use of compressed medical gas cylinders in the method of the invention, and this provides a number of advantages to the user. Such gas cylinders contain defined gas mixtures for specific medical uses, such cylinders offer the most efficient way to provide gases for use in clinical settings and such cylinders allow the user to store large volumes of gas in a relatively small space. Compressed gas cylinders typically contain gases at very high pressures. Delivery of the gas can be controlled by a valve or a gas pressure regulator. This ensures that the method is carried out under safe conditions that do not endanger the wellbeing of the user. In a particular embodiment the gas is delivered at a pressure between 0.9 bar and 2.0 bar absolute. This provides a safe gas pressure while also ensuring that gas is effectively delivered to the foam producing structure to produce foam.

In a method of the invention it is advantageous to provide continuous delivery of liquid and gas to the foam producing structure. This permits continuous combination of the liquid and gas so that constant foam production is achieved by ensuring that liquid and gas are completely combined in small increments to avoid localised pooling of insufficiently mixed liquid and gas. The user can select suitable liquid and gas flow rates to produce a required volume of foam having the appropriate properties to treat a specific indication. Liquid can be delivered at a flow rate of between 2 ml/min and 15 ml/min and preferably between 5 ml/min and 10 ml/min. This is advantageous as it permits production of foam at a sufficiently fast rate while also being within the parameters of commercially available pumps including peristaltic and volumetric pumps. Gas can be delivered at an appropriate flow rate to allow production of foam with desired properties. Typical gas flow rates are between 7 ml/min and 75 ml/min. This permits continuous production of foam within the operating parameters of commercially available pumps. Preferably the volumetric ratio of gas to liquid delivered to the foam producing structure is between 10:1 and 4:1. This allows the user to control the relative amounts of liquid and as being combined and therefore to produce foam that is effective as a therapeutic composition. Preferably the density of the foam produced using a method of the invention is between 0.07 g/ml and 0.19 g/ml, and even more preferably between 0.09 g/ml and 0.16 g/ml.

In a second aspect, the present invention provides a device for producing injectable foam comprising a foam producing structure in which liquid and gas are combined to produce foam, the structure comprising an inlet for liquid and gas and an outlet for foam; a liquid pathway in communication with the inlet; and a gas pathway in communication with the inlet, characterised in that the liquid pathway comprises a means for delivering liquid through the liquid pathway independently of gas delivery through the gas pathway.

The second aspect provides a device in which the method of the first aspect can be carried out. Liquid and gas are delivered to a foam producing structure independently, and this allows the user to adjust the proportions of liquid and gas being combined to produce foam. The arrangement of the device provides the user with all of the advantages of the method of the first aspect as described above. Regulating the delivery of liquid to the foam producing structure independently of the delivery of gas, for example by increasing or decreasing the rate of liquid delivery while holding the rate of gas delivery constant, allows for adjustment of the properties of foam as needed. Additionally, adjustment of the independent delivery of liquid, for example by replacement of or diversion to an alternative source of liquid, allows for adjustment of the properties and/or the concentration of foam as needed.

The foam producing structure provides a means for combining liquid and gas to form foam by disrupting and/or restricting the flow of each as described above. The structure provides an inlet for liquid and gas that allows for independent delivery of liquid and gas into the interior of the foam producing structure where they are combined to produce foam. Preferably the liquid and gas are independently delivered to the structure through a single inlet. This allows for mixing of the liquid and gas prior to being combined within the structure to produce foam which can aid foam formation. Alternatively, an inlet for liquid and gas can provide multiple inlets including, for example, separate inlets through which liquid and gas are separately delivered into the foam producing structure. This may be preferable where liquid and gas are to be introduced into the structure in larger volumes or at increased rates or at greatly different pressures. Additionally, separate inlets for liquid and gas may be preferred where mixing prior to being combined to produce foam is to be avoided. The structure also provides an outlet for foam. The outlet allows removal of foam produced by combination of liquid and gas within the structure for use in sclerotherapy. Preferably the outlet is at ambient atmospheric pressure, and this permits foam to leave the structure by simple volumetric displacement as further liquid and gas are delivered independently through the inlet.

The liquid pathway comprises a conduit for delivery of liquid to the inlet of the foam producing structure. Typically this conduit comprises a medical-grade polymer tube that is impermeable and inert to the liquid being delivered as well as being biocompatible. Preferably the conduit is inelastic. This means that it is essentially resistant to being deformed under the normal operating pressures of the device. In particular embodiments the conduit comprises a deformable portion. Such a deformable portion allows for engagement with an external mechanical means, for example a peristaltic pump that can deform that portion of the conduit to drive liquid through the pathway to be delivered to the foam producing structure. Suitable materials for such tubing are well known in the art and include silicones, polyvinyl chloride (PVC), and latex rubber. Suitable tube dimensions can be determined based on the volumes of liquid to be delivered but are typically within the range of 2 mm to 10 mm internal diameter. Preferably the internal diameter is between 4 mm and 6 mm.

The device can further comprise a source of foamable liquid arranged for the introduction of liquid into the liquid pathway. This simplifies use of the device by avoiding the need to charge the device with liquid from a separate container. The source of liquid can be a sealed container. This allows a sterile environment to be maintained for liquid within the device. Examples of suitable sealed containers are well known in the art and include ampoules, carpoules or traditional pharmaceutical vials that can be connected to the device through a screw top attachment or a vial spike. Optionally, the source of foamable liquid can be a pre-filled syringe.

The liquid pathway comprises a means for delivering liquid through the liquid pathway independently of gas delivery through the gas pathway. This means may be in any form suitable for the delivery of liquid to the foam producing structure provided that it operates independently of gas delivery. Such independent operation can include the provision of an independent or separate force to deliver liquid, and it can also include the independent or separate control or programming of such a force. Such a means can be a system for pressurisation of a source of foamable liquid arranged for the introduction of liquid into the liquid pathway. Pressurisation of a liquid source provides for liquid delivery without requiring inclusion of significant mechanical equipment or moving parts. Preferably the means for delivering liquid through the liquid pathway is a pump, for example a peristaltic pump. Most preferably the pump is a volumetric pump. The use of a pump or a volumetric pump as the means for delivering liquid delivers al of the advantages discussed above with respect to the use of pumps in a method of the first aspect of the invention. The device may also include a motor arranged to drive a pump. Such a motor is any device that can drive the pump, and can include a motor that engages a pump mechanically or magnetically. Engagement of the pump may be direct (i.e. the motor contacts the pump directly) or indirect (i.e. the motor contacts the pump through an intermediary structure), for example through a drivetrain. Inclusion of a pump within the device allows for the device to be self-contained and simplifies control of liquid delivery as no external motor need be attached to the device for use.

Optionally, the liquid pathway comprises a one-way valve or a back pressure valve. This prevents reflux or backward flow of liquid within the liquid pathway. Prevention of reflux is particularly important in that it allows a liquid source to be changed while the device is in use. It will be understood that the valve may be located at any point in the in the liquid pathway, but preferably a valve is situated between the means for delivering liquid and the foam producing structure.

The gas pathway comprises a conduit for delivery of gas to the inlet of the foam producing structure. Typically this conduit comprises a medical-grade polymer tube that is impermeable and inert to the gas being delivered as well as being biocompatible. The conduit is inelastic. This means that it is essentially resistant to being deformed under the normal operating pressures of the device. This permits the user to deliver gas to the foam producing structure under pressure without gas being retained within an expanding or deforming conduit. Suitable materials for such tubing are well known in the art and include silicones, polyvinyl chloride (PVC), and latex rubber. Suitable tube dimensions can be determined based on the volumes of liquid to be delivered but are typically within the range of 2 mm to 10 mm internal diameter. Preferably the internal diameter is between 4 mm and 6 mm.

The device can further comprise a source of gas arranged for the introduction of gas into the gas pathway. This simplifies use of the device by avoiding the need to charge the device with gas from a separate container. The source of gas can contain compressed gas or gas at atmospheric pressure. Preferably the source of gas is a compressed gas cylinder. Such gas cylinders can be provided containing defined gas mixtures for specific medical uses, and such cylinders offer the most efficient way to provide gases for use in clinical settings and such cylinders allow the user to store large volumes of gas in a relatively small space. Compressed gas cylinders typically contain gases at very high pressures. The use of a compressed gas cylinder additionally provides potential energy to deliver the gas into the foam producing structure and to drive combination of liquid and gas to produce foam. Delivery of the gas can be controlled by a valve or a gas pressure regulator. A regulator ensures that the gas is introduced to the gas pathway at a suitable pressure that is safe and that is sufficient to produce foam. A valve prevents reflux or reverse flow of gas or liquid within the liquid pathway. Prevention of reflux is advantageous in allowing changing of gas cylinders while the device is in use. Preferably the delivery of gas is controlled by a gas pressure regulator and a valve.

Optionally, the gas pathway can comprise a pump, for example a peristaltic pump. Most preferably the pump is a volumetric pump. The use of a pump or a volumetric pump to deliver gas provides all of the advantages discussed above with respect to the use of pumps in a method of the first aspect of the invention. The device may also include a motor arranged to drive the pump. Such a motor can engage the pump mechanically or magnetically. Engagement of the pump may be direct (i.e. the motor physically contacts the pump directly), or it may be indirect (i.e. the motor does not physically contact the pump), for example magnetically or through a drivetrain. Inclusion of the pump within the device allows for the device to be self-contained and simplifies control of gas delivery as no external motor need be attached to the device for use.

Optionally, the gas pathway comprises a gas-sterilising filter. This ensures that gas entering the foam producing structure is sterile as required for the production of foam for clinical use.

The device can further comprise a foam port connected to the outlet for foam by a foam pathway. The foam pathway provides a conduit between the outlet and the foam port such that foam produced in the foam producing structure is delivered to the foam port for collection by the user of the device. The foam allows connection of standard medical devices such as syringes or catheters to the device. In a preferred embodiment the foam port is suitable for engaging with a standard syringe Luer slip.

The foam pathway may optionally comprise a foam conditioning structure. The foam conditioning structure provides a number of additional elements similar to those provided in the foam producing structure. Passing of foam through these additional elements ensures that bubble size distribution within the foam is limited and that large bubbles are removed. The foam conditioning structure can be situated close to the outlet or close to the foam port or at any point between the two ends of the foam pathway.

It will be understood that before and between uses the device will contain dead space or air such that initial delivery of liquid and gas to the foam producing structure can lead to production of initial foam that is outside the intended specification, and it is necessary to discard such initial foam. Optionally, the device can comprise a waste chamber. The waste chamber is in communication with the foam pathway and is arranged such that it retains this initial foam so that it is not administered to a patient. Typically, the waste chamber will vent to air, and initial foam will be diverted into the waste chamber by the opening of a valve. Alternatively initial foam flows into the waste chamber, and flow of foam is then diverted to the foam pathway by a pressure-sensitive valve that prevents it entering the waste chamber. Alternatively the pressure that must be overcome by initial foam entering the waste chamber is lower than the pressure that foam must overcome to pass through the foam pathway.

Preferably, the device is provided in a form such that key components are provided as a disposable cartridge, consumable or cassette. A disposable arrangement optimises device use and reduces the likelihood of user error in producing foam. Additionally, disposable use improves the flexibility offered to the user by making adjustment of foam concentration easier and safer. In its simplest form such a disposable includes a foam producing structure having an inlet for liquid and gas and an outlet for foam, a gas pathway and a liquid pathway comprising a pump. Pumps can be provided inexpensively, and use of such a disposable offers the user flexibility in producing foam having desired properties. The disposable can also comprise a source of liquid. This arrangement removes the need to charge a device with liquid and offers the user security of knowing that liquid is provided in sterile condition for use in that device. The source of liquid may be provided in communication with the liquid pathway or it may be sealed and require activation to provide liquid to the pathway. Such activation may break a seal, for example by deployment of a vial spike, or it may engage a threaded engagement means. Activation of a sealed source of liquid allows the user to record the opening date of the source and therefore more accurately determine the usable life of the product.

Additionally, the disposable can comprise a foam port connected to the outlet for foam by a foam pathway. This allows the user to withdraw foam directly from the disposable such that all components that contact the foam directly can be discarded after use, thereby removing the risk of foam contamination.

Optionally, the disposable can comprise a waste chamber in communication with the foam pathway. This simplifies use for the user by removing the need to manually discard waste foam or gas produced on initial operation. Preferably, the foam pathway includes a waste valve that controls communication with the waste chamber. This allows reliable control of the amount of waste discarded and ensures that usable foam is not wasted.

Optionally, the gas pathway can also comprise additional components including, for example, a pump or a gas sterilising filter. Including a pump in the gas pathway allows the user to more closely control the rate of delivery of gas to the foam producing structure. Inclusion of a gas sterilising filter allows the user to change gas source infrequently while ensuring that gas is sterile on delivery to the foam producing structure. Preferably the gas pathway can comprise a pump and a gas sterilising filter.

In a preferred embodiment the disposable comprises a foam producing structure having an inlet for liquid and gas and an outlet for foam, a gas pathway, a liquid pathway comprising a pump, a source of liquid, a foam port connected to the outlet for foam by a foam pathway and a waste chamber in communication with the foam pathway.

Preferably the disposable cartridge, consumable or cassette is used to produce foam by engaging with a durable machine that controls the means for delivering liquid through the liquid pathway independently of gas delivery through the gas pathway. This offers flexibility for the user who can switch between such disposable devices in order to produce various foams in the clinic with a single machine. In preferred embodiments the disposable cartridge, consumable or cassette engages with the machine by a mechanical interference fit formed by the user pushing it into a suitably engineered interface within the machine. Such a mechanism simplifies installation and removal of the disposable so that the user can rapidly and easily replace or change them as required. The disposable cartridge, consumable or cassette can be engaged with the machine by locking of an engaging mechanism. This prevents unintended removal of the cassette from the machine while in use, thereby improving safety of use in producing foam.

In this durable machine/disposable cassette format the machine can comprise a control unit. The control unit controls the means for delivering liquid to the foam producing structure, and therefore it controls the characteristics of foam produced using the device. The control unit can be a mechanical component, for example a timer that controls the duration of liquid delivery through the liquid pathway. This provides a simple and inexpensive way for the user to control foam production using the device. Preferably the control unit is computerised, for example a computerised component that directly regulates the speed of a pump delivering liquid through the liquid pathway. This provides a sophisticated control mechanism that allows the user to control foam production while avoiding potential volume limitations or restrictions that a timer control unit would impose. More preferably the control unit comprises a CPU.

The machine can comprise a bubble-sizer configured to measure bubble size distribution in the foam pathway. This can confirm appropriate bubble size distributions for the user as well as providing an alert should foam be produced that is not within the required specification. Optionally, the bubble-sizer comprises thermal elements, optical elements, resistive elements, capacitive elements, ultrasound elements or a camera to determine bubble size. Preferably, the foam monitoring means comprises a camera. Operation of such a camera bubble-sizer would require that a portion of the foam pathway where size determination was to be carried out is translucent and of sufficiently small internal diameter to permit passage of singled bubbles through the field of view of the camera. This provides a simple and direct optical system for bubble size determination. Preferably, operation of the bubble-sizer is controlled by the control unit. This allows automation of operation and offers the possibility of automated foam quality monitoring within the machine.

The invention will now be described further with reference to the accompanying drawings, in which.

EXAMPLES

Figure 1A:
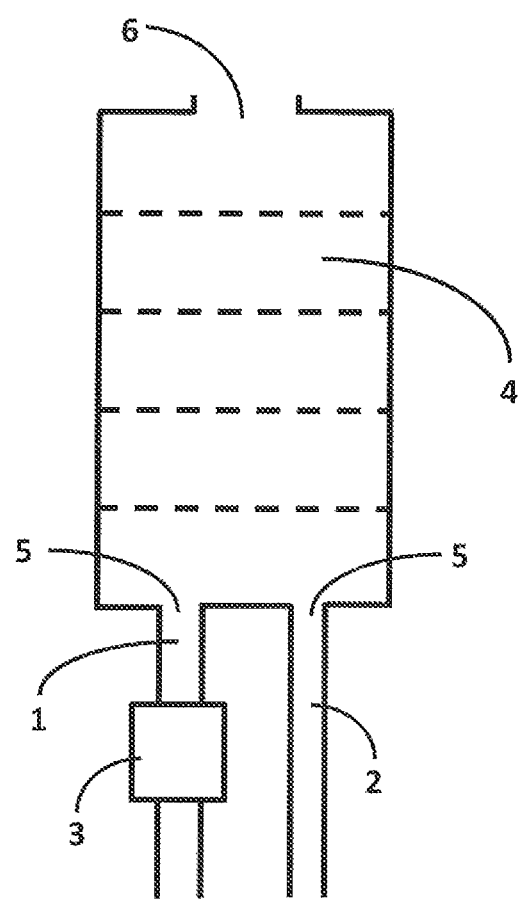
FIGS. 1A and 1B shows a schematic view of the key components necessary to produce foam according to the method of the invention.
Figure 1B:
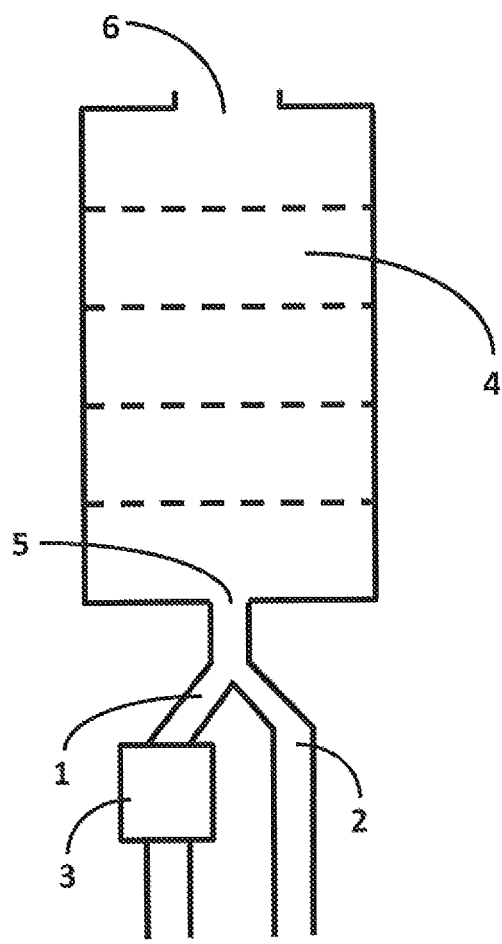

FIGS. 1A and 1B show schematic views of the key components of the invention in which a foam producing structure (4) is shown having an inlet for liquid and gas (5) and an outlet for foam (6). A liquid pathway (1) is in communication with an inlet (5), and a gas pathway (2) is in communication with a separate inlet (5). A pump (3) is provided within the liquid pathway (1).

The device comprises a minimal combination of structural features necessary to produce foam according to the invention, and therefore it is particularly suitable for use as a disposable device in combination with a machine that drives the pump (3) and provides sources of liquid and gas.

Figure 2:
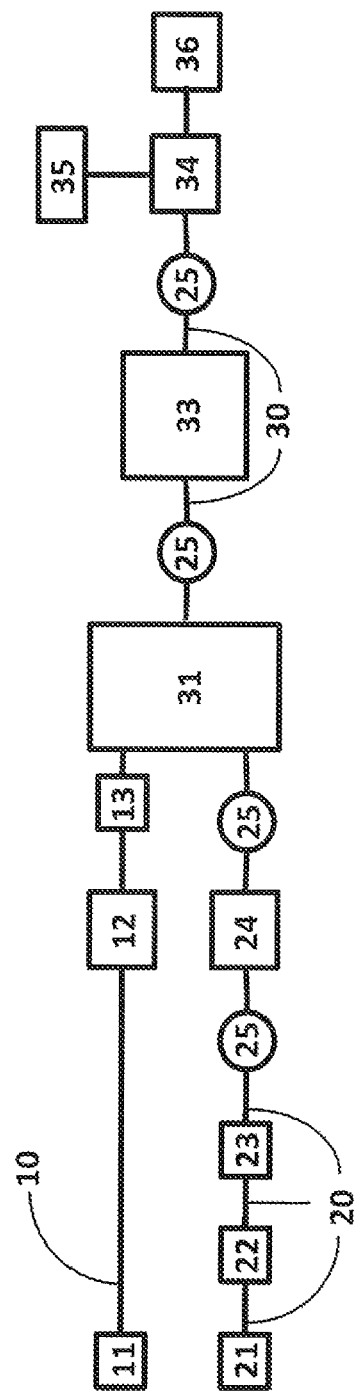
FIG. 2 shows a schematic view of a combination of components that may be used to produce foam according to the method of the invention.

FIG. 2 shows a schematic view of a combination of components that may be used to produce foam in which a liquid pathway (10) and a gas pathway (20) are in communication with a foam producing structure (31) through separate inlets for liquid and gas (not identified in the drawing). In this example the foam producing structure (31) includes a mesh stack. The liquid pathway (10) and the gas pathway (20) each comprise silicone tubing.

Gas is provided to the gas pathway (20) from an external pressurised gas source (not shown) through a gas connector (21) at a pressure that is controlled by an external gas pressure regulator (not shown) arranged inline between the pressurised gas source (not shown) and the gas connector (21).

Gas passage through the gas pathway (20) is controlled by a gas valve (22) that may be open or closed. When the gas valve (22) is open during use of the device gas passes through a gas filter (23) to ensure that gas provided to the foam producing structure (31) is sterile. Sterile gas is delivered to the foam producing structure (31) through the gas pathway (20) by a gas pump (24). The gas pump (24) is a volumetric pump that propels 20 µl of gas with each pump stroke. Adjustments can be made to the rate or frequency of operation of the gas pump (24) so as to deliver a desired volume of gas to the foam producing structure (31).

Pressure sensors (25) are provided in the gas pathway (20) to measure gas pressure on entry to the gas pump (24) and on entry to the foam producing structure (31). Gas pump (24) operation typically increases gas pressure before entry to the foam producing structure (31).

Liquid is provided to the liquid pathway (10) from an external liquid source (not shown) through a liquid connector (11) at ambient pressure and propelled through the liquid pathway (10) by a liquid pump (12) that operates independently of the gas pathway (20) and the gas pump (24). The liquid pump (12) is a volumetric pump that propels 5 µl of gas with each pump stroke. Adjustments can be made to the rate or frequency of operation of the liquid pump (12) so as to deliver a desired volume of liquid to the foam producing structure (31). A back pressure valve (13) is located between the liquid pump (12) and foam producing structure (31) to prevent liquid reflux in the liquid pathway (10).

Liquid and gas are independently delivered to the foam producing structure (31) where they mix and pass across a series of 4 mesh filters having a mean pore size of 5 µm with the filters being separated from each other by between 3.5 mm and 3.7 mm to produce foam. Foam produced in the foam producing structure (31) is delivered to the foam pathway (30) through the outlet. The foam is then passed through a foam conditioning structure (33) which comprises a further mesh stack of 4 filters, each having a mean pore size of 5 µm, and the filters being separated from each other within the stack by between 3.5 mm and 3.7 mm (Filtertek). Passage through the foam conditioning structure (33) yields steady state foam with increased stability compared to foam that is not passed through the foam conditioning structure (33).

Optimal quality foam is separated from inferior quality foam produced on initial operation of the device by activating a waste valve (34) arranged within the foam pathway (30) to control communication between the foam pathway (30) and a waste chamber (35). Opening the waste valve (34) allows communication between the waste chamber (35) and the foam pathway (30) to allow a portion of foam to be diverted into and retained within the waste chamber (35). The waste valve (34) is closed once optimal quality foam is produced, and foam is provided through the foam pathway (30) to the foam port (36) for use by the user.

Pressure sensors (25) are provided in the foam pathway (30) to measure foam pressure on exit from the foam producing structure (31) and on exit from the foam conditioning structure (33). Foam pressure is reduced to ambient pressure on exit from the foam conditioning structure (33).

Figure 3:
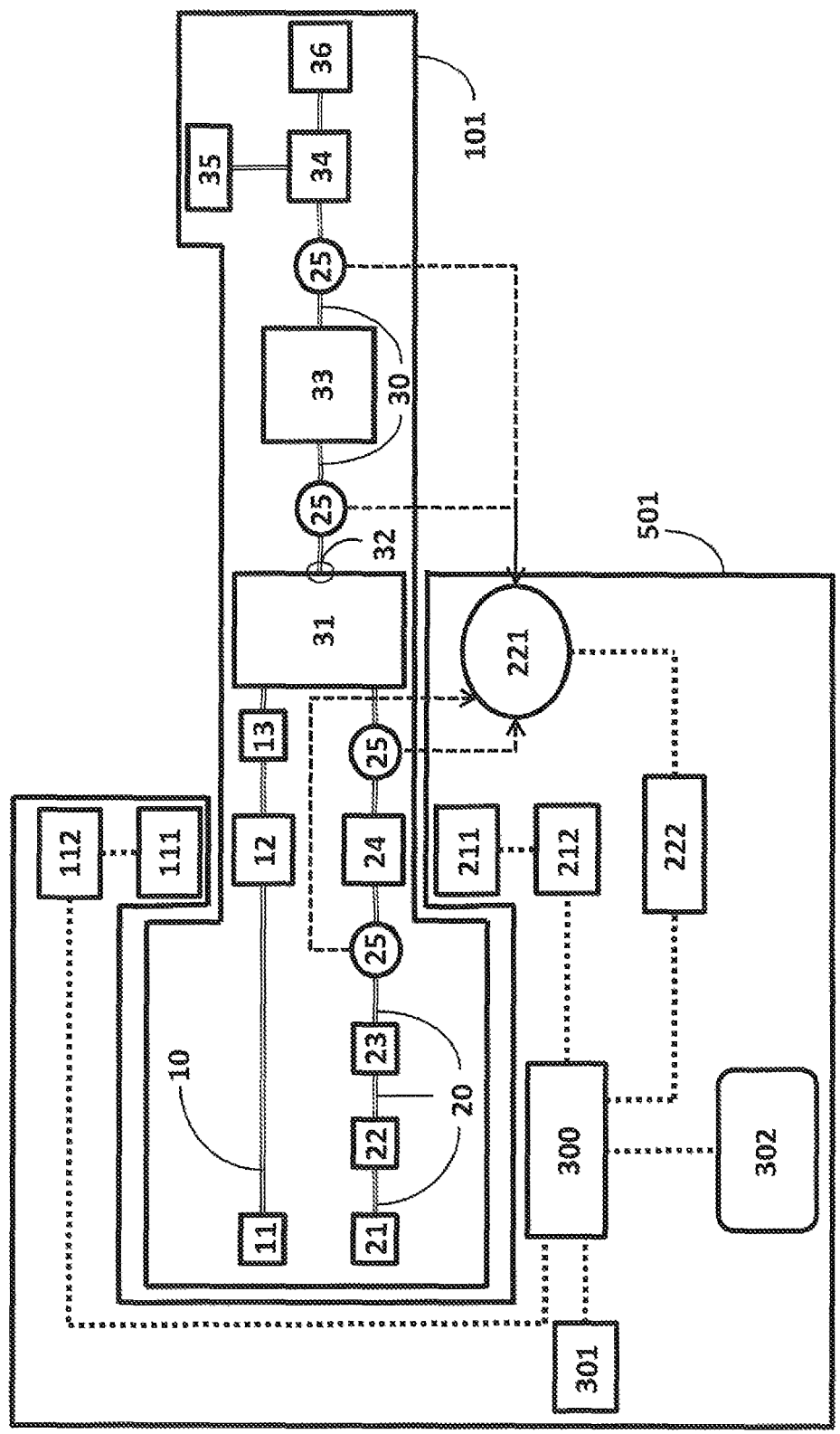
FIG. 3 shows a schematic view from the combination of components from FIG. 2 engaged with additional components that may be provided in a durable machine.
Figure 4:
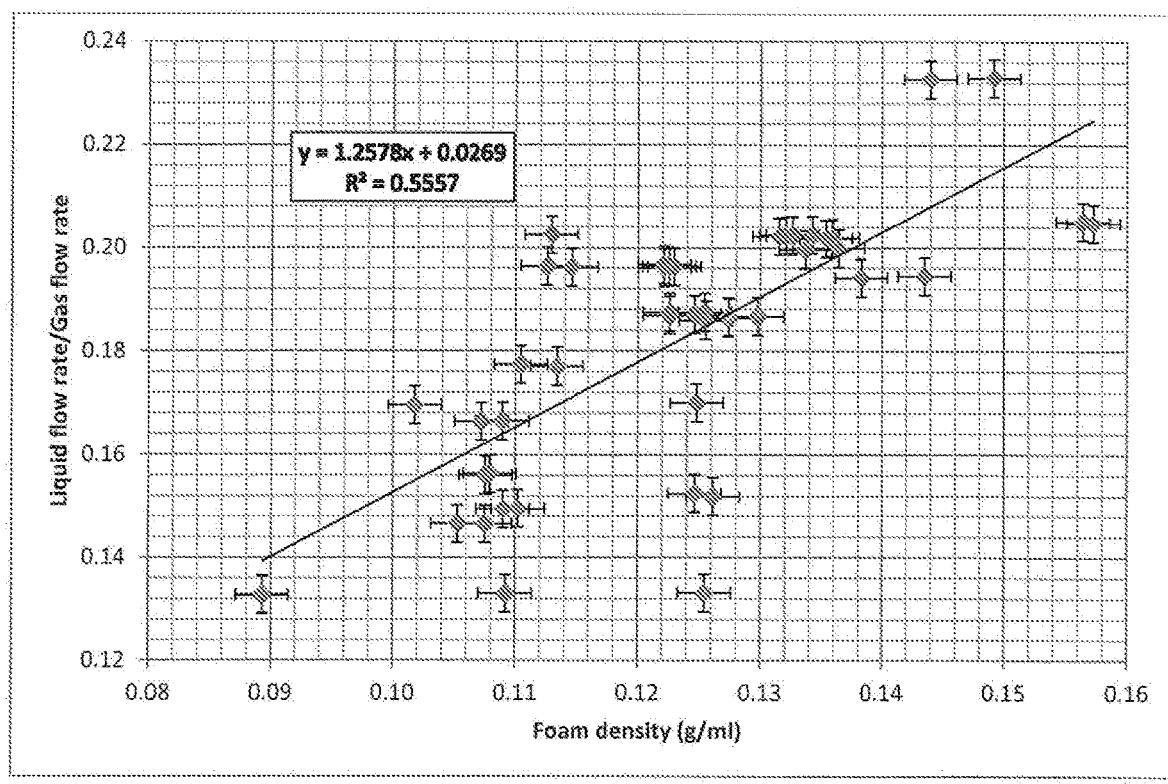
FIG. 4 shows a graph of the Liquid flow rate:Gas flow rate ratio against foam density obtained using a device of the invention. The data used are presented in tabular form in Table 2.
Figure 5A:
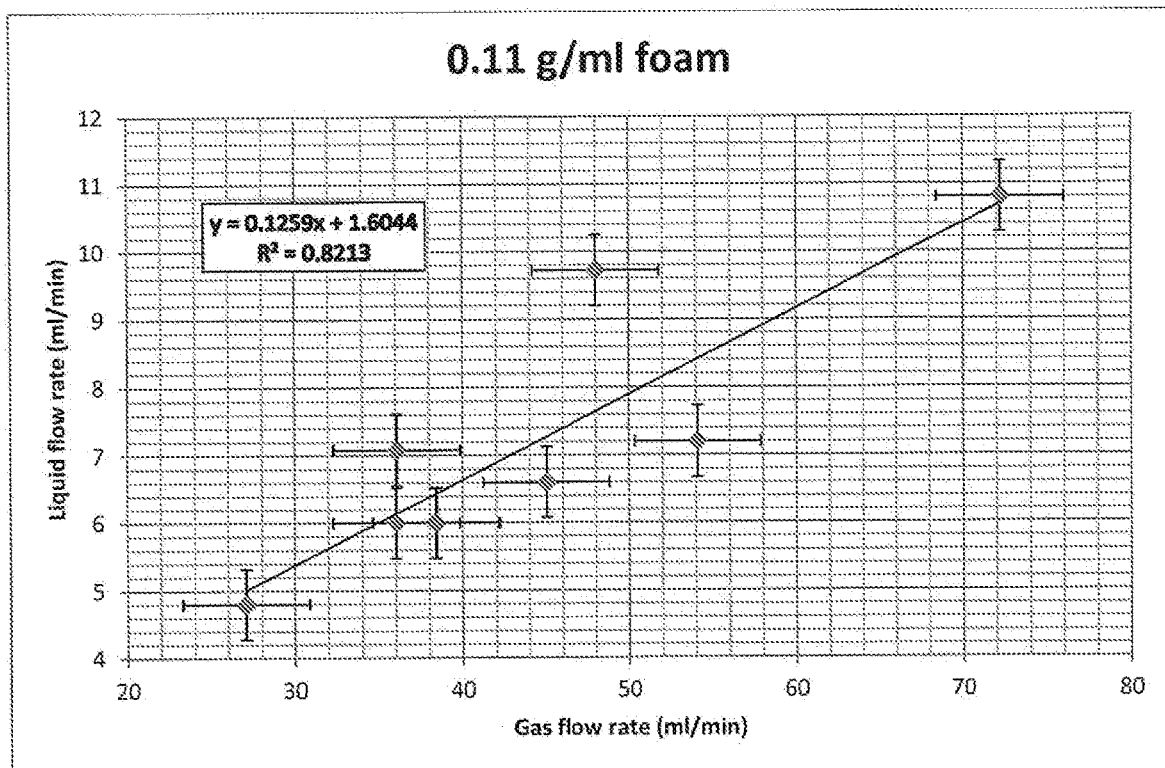
FIGS. 5A to 5D show graphs of Liquid flow rate against Gas flow rate for production of foam having densities of 0.11 g/ml, 0.12 g/ml, 0.13 g/ml and 0.14 g/ml respectively using a device of the invention. The data used are presented in tabular form in Table 2.
Figure 5B:
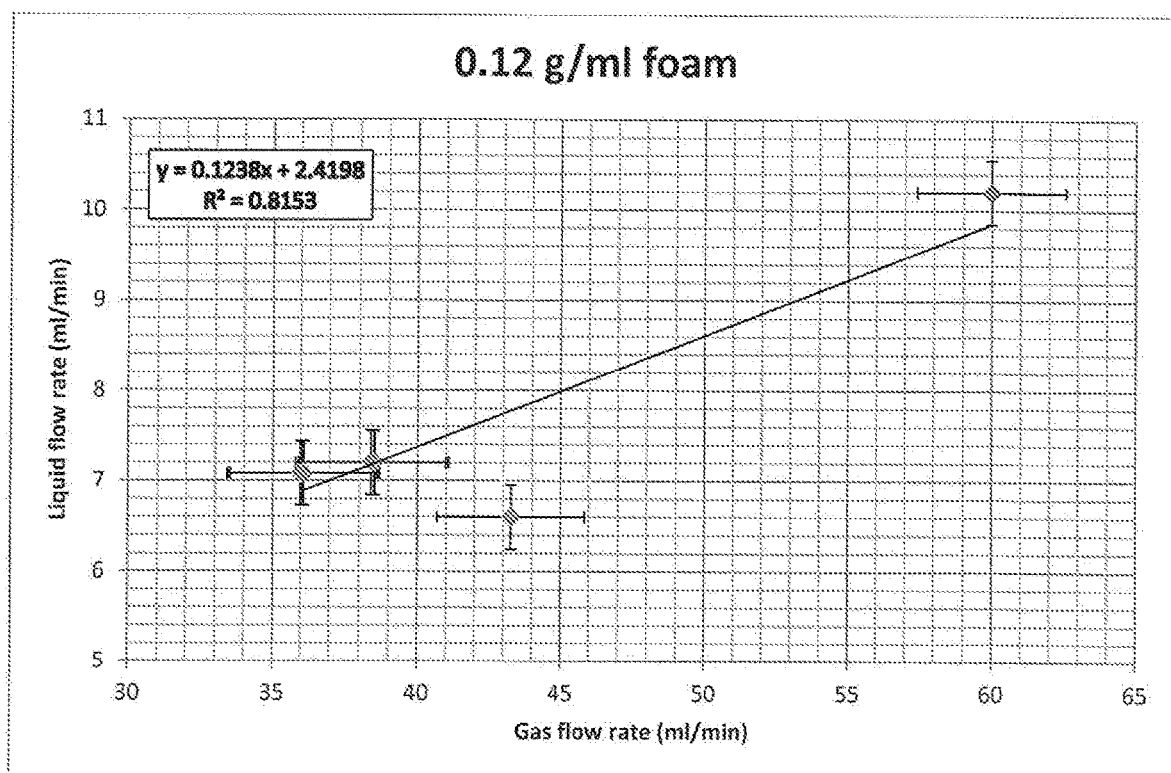
Figure 5C:
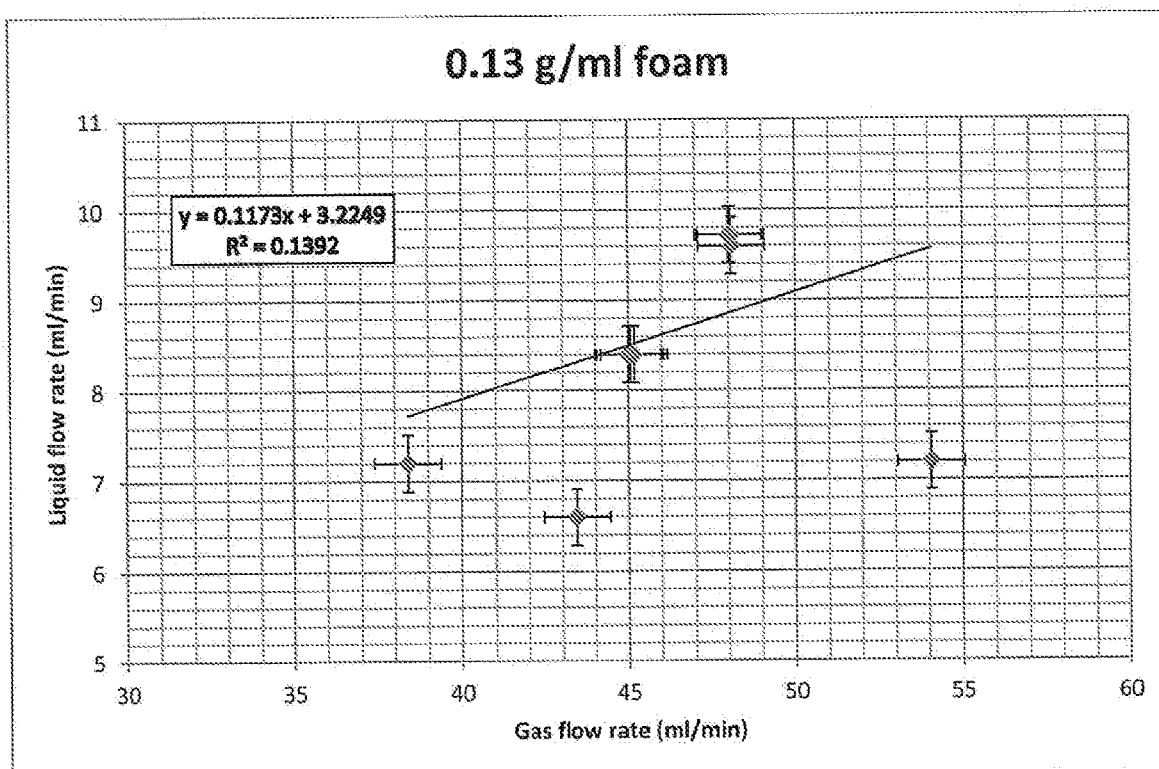
Figure 5D:
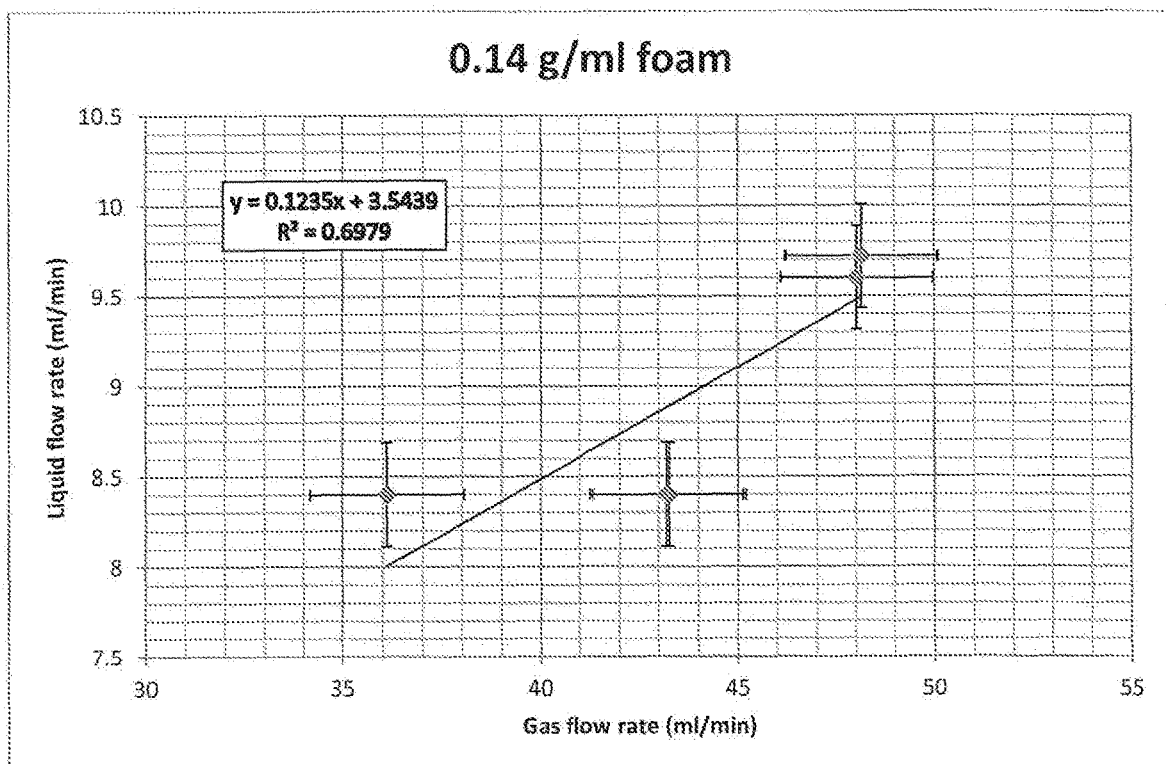

FIG. 3 shows a schematic view of the combination of components from FIG. 2 in the form of a disposable (101) engaged with additional components likely provided in a durable machine (501). In this scheme a liquid pump motor (111) and a gas pump motor (211) are arranged to engage and drive the liquid pump (12) and the gas pump (24) respectively so as to deliver liquid and gas independently to the foam producing structure (31) where they are combined to produce foam as described in FIG. 1. The user defines the foam specification required and programmes the apparatus using a data input device (302), which is a 7" touchscreen device arranged in electronic communication with a control unit (300).

The control unit (300) is a programmable computer device arranged in electronic communication with a liquid pump motor controller (112) and a liquid pump motor (111) which mechanically engages the liquid pump (12). The user provides instruction to the control unit (300) through the data input device (302) instructing the liquid pump motor controller (112) to operate the liquid pump motor (111) at a defined speed. The liquid pump motor (111) then drives the liquid pump (12) at the defined speed so as to deliver liquid through the liquid pathway (10) to the foam producing structure (31) independently of the delivery of gas through the gas pathway (20).

The control unit (300) is similarly and independently arranged in electronic communication with a gas pump motor controller (212) and a gas pump motor (211) which mechanically engages the gas pump (24). The user provides instruction to the control unit (300) through the data input device (302) instructing the gas pump motor controller (212) to operate the gas pump motor (211) at a defined speed. The gas pump motor (211) then drives the gas pump (24) at the defined speed so as to deliver gas through the gas pathway (20) to the foam producing structure (31) in the required amount.

The device also includes a pressure sensor system (221) arranged in electronic communication with pressure sensors (25) located in the gas pathway (20) and in the foam pathway (30). The pressure sensor system (221) is in electronic communication with an analog measurement system (222) and provides pressure readings from the pressure sensors (25) to the analog measurement system (222). Pressure readings are standardised and provided to the control unit (300) where they are stored and can then be monitored by the user on the data input device (302).

The apparatus further includes a data interface (301) that allows the user to download data and information form the control unit (300). In this example the data interface (301) is a USB connector.

Table 1 describes the characteristics of foam produced under varied conditions using a device of the invention as shown in FIG. 3. The liquid used was a 1% (w/v) aqueous solution of polidocanol, and the gas used was a mixture of oxygen (65%) and carbon dioxide (35%).

Table 2 describes production of foam having defined density using a device of the invention comprising the combination of components as shown in FIG. 3. The liquid used was a 1% (w/v) aqueous solution of polidocanol, and the gas used was a mixture of oxygen (65%) and carbon dioxide (35%). The data are presented in graphic form in FIGS. 4 and 5A to 5D. These data demonstrate that foam having desired properties can be produced using a method and a device of the inventions under various conditions that influence the density and production rate of foam.

Figure 6:
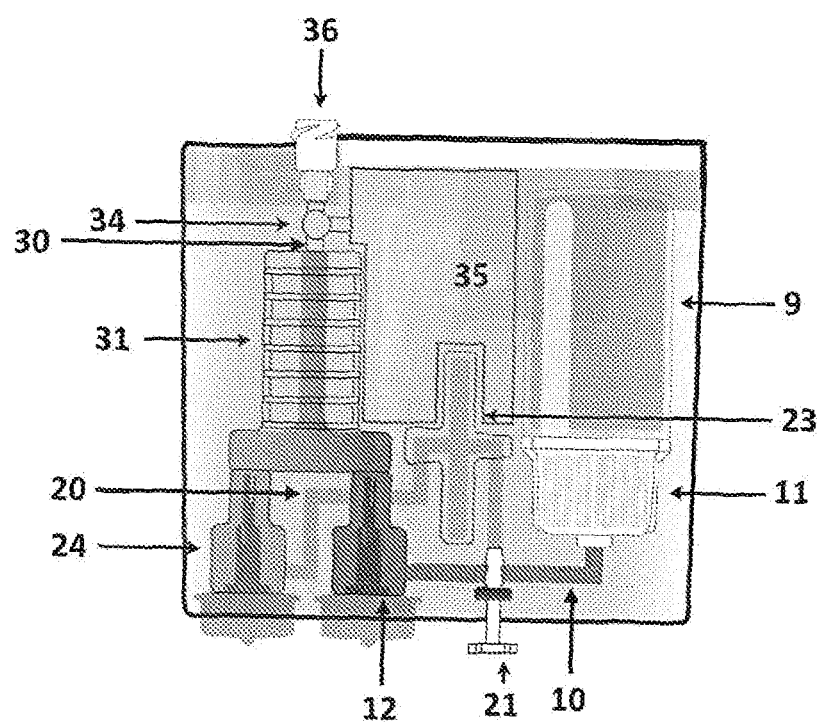
FIG. 6 shows a section view of a device according the invention.

FIG. 6 shows a section view of a disposable component of the device according to the second aspect of the invention. An external source of gas (not shown) is arranged in communication with a gas connector (21) to provide gas to a gas pathway (20). Gas is delivered through the gas pathway (20) to a foam producing structure (31) by a gas pump (24). A source of liquid (9) in the form of a vial is arranged in communication with a liquid connector (11) in the form of a vial spike to provide liquid to a liquid pathway (10). Liquid is delivered through the liquid pathway (10) to the foam producing structure (31) by a liquid pump (12). Liquid and gas are combined in the foam producing structure (31) to produce foam, which then enters a foam pathway (30). Initial poor quality foam is diverted into a waste chamber (35) together with any gas to be purged from the device by activating a waste valve (34) to open communication between the foam pathway (30) and the waste chamber (35). The waste valve (34) is then closed and foam for use in sclerotherapy is delivered to a foam port (36).

Figure 7:
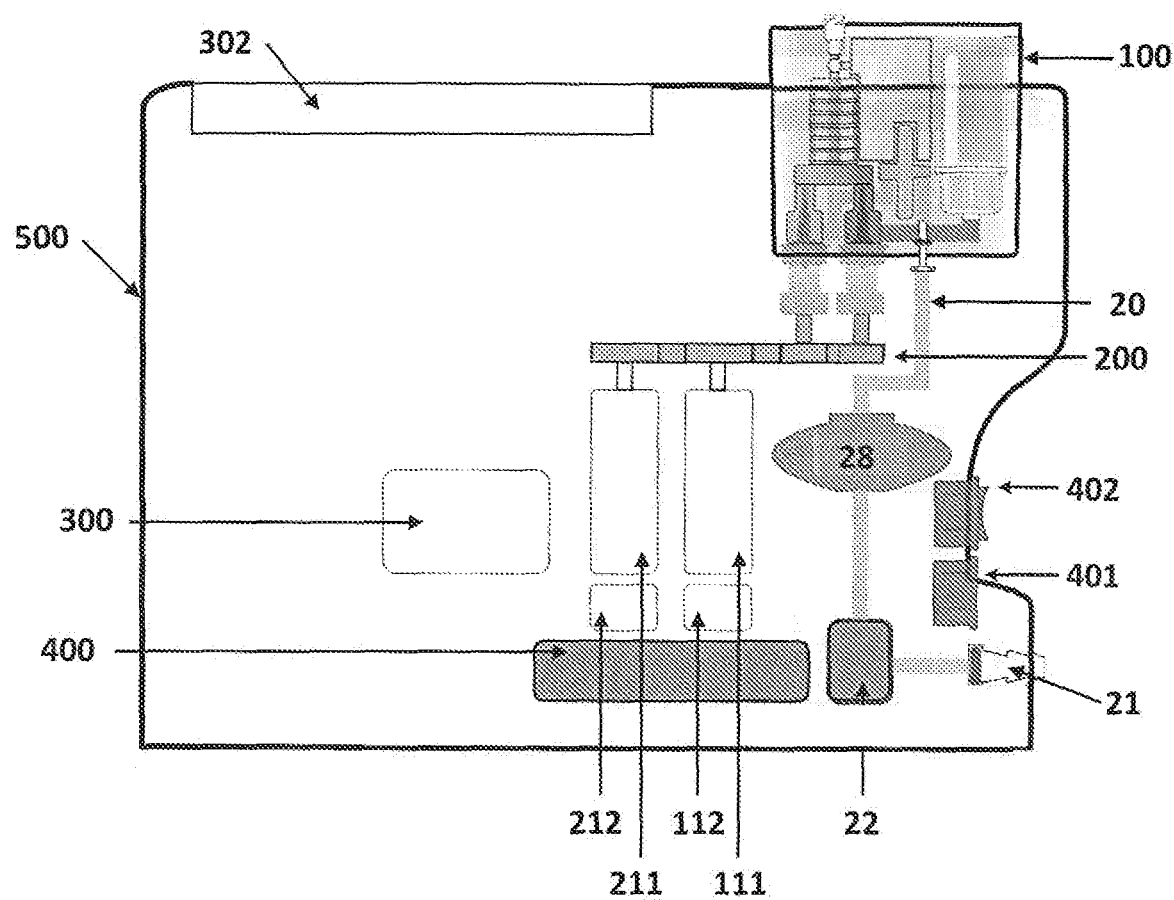
FIG. 7 shows a section view of a device according to the invention incorporating the device of FIG. 6.

FIG. 7 shows a section view of a device according to the second aspect of the invention in which the disposable component of FIG. 6 (100) is engaged with a durable machine (500) to produce foam.

Electrical power is supplied to the machine (500) through a mains input (401) to provide electricity to the power supply (400). A power switch (402) is used to engage (on) and disengage (off) electrical power to the device through the mains input (401). The power supply provides the appropriate electrical power supply to a control unit (300) to control operation of the device.

The control unit (300) is in electrical communication with a liquid pump motor controller (112) that controls a liquid pump motor (111). The pump motor (111) indirectly engages and drives a liquid pump to deliver liquid through the liquid pathway into the foam producing structure within the disposable component (100). The indirect engagement between the pump motor (111) and the pump is mediated by a drivetrain mechanism (200).

An external source of gas (not shown) is arranged in communication with a gas connector (21) to provide gas to a gas pathway (20) that includes a gas valve (22) and a gas pressure regulator (28). Gas is delivered through the gas pathway (20) to the disposable component (100) as described in FIG. 6.

The control unit (300) is independently in electrical communication with a gas pump motor controller (212) that controls a gas pump motor (211). The pump motor (211) indirectly engages and drives a gas pump to deliver gas through the gas pathway into the foam producing structure within the disposable component (100). The indirect engagement between the pump motor (211) and the pump is mediated by a drivetrain mechanism (200). The drivetrain mechanism (200) mediates engagement of the liquid pump independently from engagement of the gas pump thereby providing independent delivery of liquid and gas to the foam producing structure within the disposable device (100).

The user defines the foam specification required and programmes the apparatus using a data input device (302) that is arranged in electronic communication with the control unit (300). User programming of the control unit (300) through the data input device (302) instructs the motor controllers (112, 212) to operate the pump motors (111, 211) at defined speeds and thereby deliver liquid and gas to the foam producing structure within the disposable component (100).

TABLE 1

| Gas pump speed[#] (Hz) | Liquid pump[♦] speed (Hz) | Gas flow rate (ml/h) | Liquid flow rate (ml/hr) | Pressure* (bar) | Foam half-life (s) | Foam density | Syringe fill time (s) |
|---|---|---|---|---|---|---|---|
| 6 | 18 | 432 | 324 | 2.232 | 149 | 0.178 | 65 |
| 10 | 18 | 720 | 324 | 2.216 | 149 | 0.113 | 42 |
| 6 | 12 | 432 | 216 | 2.239 | 148 | 0.140 | 76 |
| 6 | 16 | 432 | 288 | 2.254 | 148 | 0.175 | 66 |
| 8 | 18 | 576 | 324 | 2.214 | 157 | 0.133 | 46 |
| 8 | 10 | 576 | 180 | 1.230 | 142 | 0.143 | 89 |
| 8 | 8 | 576 | 144 | 1.221 | 156 | 0.129 | 88 |
| 12 | 10 | 864 | 180 | 0.638 | 142 | 0.191 | 103 |
| 6 | 8 | 432 | 144 | 2.256 | 166 | 0.094 | 69 |

[#]20 μl volumetric pump
[♦]5 ml volumetric pump
*pressure measured before entry of gas into the gas pump.

TABLE 2

| Density (g/ml) | Gas flow rate * (ml/min) | Liquid flow rate (ml/min) | Liquid/Gas ratio |
|---|---|---|---|
| 0.09 | 27.108 | 3.6 | 0.132802 |
| 0.09 | 27.126 | 3.6 | 0.132714 |
| 0.10 | 60.15 | 10.2 | 0.169576 |
| 0.11 | 45.03 | 6.6 | 0.146569 |
| 0.11 | 36.054 | 6 | 0.166417 |
| 0.11 | 45.03 | 6.6 | 0.146569 |
| 0.11 | 38.448 | 6 | 0.156055 |
| 0.11 | 38.376 | 6 | 0.156348 |
| 0.11 | 36.036 | 6 | 0.1665 |
| 0.11 | 72.252 | 10.8 | 0.149477 |
| 0.11 | 54.108 | 7.2 | 0.133067 |
| 0.11 | 72.216 | 10.8 | 0.149551 |
| 0.11 | 27.054 | 4.8 | 0.177423 |
| 0.11 | 36.054 | 7.08 | 0.196372 |
| 0.11 | 48 | 9.72 | 0.2025 |
| 0.11 | 27.108 | 4.8 | 0.177069 |
| 0.11 | 36.09 | 7.08 | 0.196176 |
| 0.12 | 36.108 | 7.08 | 0.196078 |
| 0.12 | 36 | 7.08 | 0.196667 |
| 0.12 | 36.054 | 7.08 | 0.196372 |
| 0.12 | 38.4 | 7.2 | 0.1875 |
| 0.12 | 38.52 | 7.2 | 0.186916 |
| 0.12 | 36.072 | 7.08 | 0.196274 |
| 0.12 | 38.496 | 7.2 | 0.187032 |
| 0.12 | 43.272 | 6.6 | 0.152524 |
| 0.12 | 60 | 10.2 | 0.17 |

TABLE 2-continued

| Density (g/ml) | Gas flow rate * (ml/min) | Liquid flow rate (ml/min) | Liquid/Gas ratio |
|---|---|---|---|
| 0.13 | 54.072 | 7.2 | 0.133156 |
| 0.13 | 38.4 | 7.2 | 0.1875 |
| 0.13 | 45.18 | 8.4 | 0.185923 |
| 0.13 | 43.452 | 6.6 | 0.151892 |
| 0.13 | 45.06 | 8.4 | 0.186418 |
| 0.13 | 45.03 | 8.4 | 0.186542 |
| 0.13 | 45 | 8.4 | 0.186667 |
| 0.13 | 48.072 | 9.72 | 0.202197 |
| 0.13 | 48.024 | 9.72 | 0.202399 |
| 0.13 | 48 | 9.72 | 0.2025 |
| 0.13 | 48.048 | 9.72 | 0.202298 |
| 0.13 | 48.09 | 9.6 | 0.199626 |
| 0.13 | 48 | 9.72 | 0.2025 |
| 0.14 | 48.168 | 9.72 | 0.201794 |
| 0.14 | 48.144 | 9.72 | 0.201894 |
| 0.14 | 48.03 | 9.6 | 0.199875 |
| 0.14 | 43.272 | 8.4 | 0.194121 |
| 0.14 | 43.2 | 8.4 | 0.194444 |
| 0.14 | 36.108 | 8.4 | 0.232635 |
| 0.15 | 36.072 | 8.4 | 0.232868 |
| 0.16 | 71.964 | 14.76 | 0.205103 |
| 0.16 | 72.072 | 14.76 | 0.204795 |

* gas flow rate normalised for pressure

The invention claimed is:

1. A method of producing injectable foam comprising:
   selecting a desired density value as a chosen parameter of the injectable foam;
   independently delivering a foamable liquid and a gas to a foam producing structure;
   passing the foamable liquid and the gas through at least one element defining at least one passage within the foam producing structure;
   independently controlling the flow rate of the foamable liquid and the gas using a control unit;
   wherein the control unit adjusts the relative amounts and flow rates of the foamable liquid and gas delivered to the foam producing structure;
   producing foam in the foam producing structure;
   passing the foam from the foam producing structure through a waste valve;
   opening the waste valve when inferior quality foam not having the chosen parameter is produced and diverting the inferior quality foam into a waste chamber;
   closing the waste valve when foam having the chosen parameter is being produced; and
   producing and dispensing the injectable foam having the chosen parameter.

2. The method according to claim 1 wherein the foamable liquid is delivered by a pump.

3. The method according to claim 2 wherein the pump is a volumetric pump.

4. The method according to claim 1 wherein the gas is delivered by a volumetric pump.

5. The method according to claim 1 wherein the gas is delivered under pressure.

6. The method according to claim 5 wherein the pressure is between 0.9 and 2.0 bar absolute.

7. The method according to claim 1 wherein the foamable liquid is delivered at a flow rate of between 7 ml/min and 10 ml/min.

8. The method according to claim 1 wherein the gas is delivered at a flow rate of between 24 ml/min and 36 ml/min.

9. The method according claim 7 wherein the volumetric ratio of foamable liquid to gas delivered to the foam producing structure is between 0.10 and 0.25.

10. The method according to claim 9 wherein the density of the injectable foam produced is between 0.09 g/ml and 0.16 g/ml.

11. The method according to claim 1, wherein selecting the desired density value includes selecting a desired density value in g/ml.

12. A method of producing injectable foam comprising:
    selecting a desired density value from a range of 0.09 g/ml to 0.16 m/ml for the injectable foam;
    independently delivering a foamable liquid and a gas to a foam producing structure;
    passing the foamable liquid and the gas through at least one element defining at least one passage within the foam producing structure;
    independently controlling the flow rate of the foamable liquid and the gas using a control unit;
    wherein the control unit adjusts the relative amounts and flow rates of the foamable liquid and gas delivered to the foam producing structure;
    producing foam in the foam producing structure;
    passing the foam from the foam producing structure through a waste valve;
    opening the waste valve when the foam being produced does not have the desired density value, and diverting the foam into a waste chamber;
    closing the waste valve when the foam being produced has the desired density value; and
    dispensing the injectable foam having the desired density value.

13. The method according to claim 12, wherein the foamable liquid is delivered by a pump.

14. The method according to claim 12 wherein the gas is delivered by a volumetric pump.

15. The method according to claim 12 wherein the gas is delivered under pressure.

16. The method according to claim 15 wherein the pressure is between 0.9 and 2.0 bar absolute.

17. The method according to claim 12 wherein the foamable liquid is delivered at a flow rate of between 7 ml/min and 10 ml/min.

18. The method according to claim 12 wherein the gas is delivered at a flow rate of between 24 ml/min and 36 ml/min.

19. The method according to claim 17 wherein the volumetric ratio of foamable liquid to gas delivered to the foam producing structure is between 0.10 and 0.25.

* * * * *